United States Patent
Braun (10) Patent No.: US 11,213,657 B2
(45) Date of Patent: Jan. 4, 2022

(54) GUIDE WIRE FOR MEDICAL DEVICES, METHOD OF USING THE GUIDEWIRE, AND METHOD FOR FORMING A COVERING ON THE GUIDEWIRE

(71) Applicant: SYMEDRIX GmbH, Deisenhofen (DE)

(72) Inventor: Michael Braun, Backnang (DE)

(73) Assignee: SYMEDRIX GmbH, Deisenhofen (DE)

( * ) Notice: Subject to any disclaimer, the term of this patent is extended or adjusted under 35 U.S.C. 154(b) by 582 days.

(21) Appl. No.: 15/953,061

(22) Filed: Apr. 13, 2018

(65) Prior Publication Data

US 2018/0369541 A1    Dec. 27, 2018

Related U.S. Application Data (63) Continuation-in-part of application No. 15/121,414, filed as application No. PCT/EP2015/053305 on Feb. 17, 2015, now abandoned.

(30) Foreign Application Priority Data

Feb. 26, 2014  (DE) .................... 20 2014 100 863.2

(51) Int. Cl.
*A61M 25/09*  (2006.01)
*A61B 5/00*   (2006.01)
(Continued)

(52) U.S. Cl.
CPC ............ *A61M 25/09* (2013.01); *A61B 5/6851* (2013.01); *A61B 90/39* (2016.02); *A61B 5/065* (2013.01);
(Continued)

(58) Field of Classification Search
CPC ........ A61M 25/09; A61M 2025/09083; A61M 2025/0008; A61M 2025/09191;
(Continued)

(56) References Cited

U.S. PATENT DOCUMENTS

| 4,922,924 A | 5/1990 | Gambale et al. |
| 5,144,959 A | 9/1992 | Gambale et al. |

(Continued)

FOREIGN PATENT DOCUMENTS

| EP | 1208868 | 5/2002 |
| EP | 1249252 | 10/2002 |

(Continued)

*Primary Examiner* — Sean P Dougherty
(74) *Attorney, Agent, or Firm* — Pandiscio & Pandiscio (57) ABSTRACT

A method for measuring a distance in a body vessel and introducing an implant into the body vessel, the method comprising: providing a guide wire, wherein the guide wire comprises a proximal end and a distal end, wherein the distal end comprises a spiral which has at least two adjoining spiral sections as markings, wherein at least a surface of one spiral section comprises a first material and at least a surface of the second spiral section comprises a second material, and further wherein the first material is different than the second material; inserting the guide wire into the body vessel; measuring the distance in the body vessel using the markings on the guide wire; and delivering the implant over the guide wire to the body vessel.

8 Claims, 10 Drawing Sheets

(51) Int. Cl.
*A61B 90/00* (2016.01)
*A61M 25/00* (2006.01)
*A61B 5/107* (2006.01)
*A61B 5/06* (2006.01)

(52) U.S. Cl.
CPC ..... *A61B 5/1076* (2013.01); *A61B 2090/3966* (2016.02); *A61M 2025/0008* (2013.01); *A61M 2025/09058* (2013.01); *A61M 2025/09083* (2013.01); *A61M 2025/09091* (2013.01); *A61M 2025/09108* (2013.01); *A61M 2025/09133* (2013.01); *A61M 2025/09166* (2013.01); *A61M 2025/09175* (2013.01); *A61M 2025/09191* (2013.01)

(58) Field of Classification Search
CPC ......... A61M 2025/09166; A61M 2025/09058; A61B 90/39; A61B 5/6851; A61B 5/1076; A61B 2090/3966
See application file for complete search history.

(56) References Cited

U.S. PATENT DOCUMENTS

| | | | |
|---|---|---|---|
| 5,209,730 A | 5/1993 | Sullivan | |
| 5,460,187 A | 10/1995 | Daigle et al. | |
| 5,984,877 A * | 11/1999 | Fleischhacker, Jr. | A61M 25/09 600/585 |
| 6,613,002 B1 * | 9/2003 | Clark | A61B 5/1076 600/104 |
| 7,811,623 B2 * | 10/2010 | Nesbitt | A61L 31/16 427/2.1 |
| 8,231,926 B2 * | 7/2012 | Nesbitt | A61L 31/10 427/2.1 |
| 8,231,927 B2 * | 7/2012 | Nesbitt | B05D 3/12 427/2.1 |
| 2002/0013540 A1 * | 1/2002 | Jacobsen | A61M 25/09 600/585 |
| 2002/0042582 A1 * | 4/2002 | Vrba | A61M 25/09 600/585 |
| 2002/0143389 A1 * | 10/2002 | St. Pierre | A61M 27/008 623/1.15 |
| 2003/0100848 A1 * | 5/2003 | Gosiengfiao | A61M 25/09 600/585 |
| 2003/0199759 A1 * | 10/2003 | Richard | A61B 6/481 600/426 |
| 2004/0186377 A1 * | 9/2004 | Zhong | A61B 90/39 600/431 |
| 2005/0015136 A1 * | 1/2005 | Ikeuchi | A61F 2/915 623/1.15 |
| 2005/0064223 A1 * | 3/2005 | Bavaro | A61B 5/6853 428/615 |
| 2005/0124917 A1 | 6/2005 | Skujins et al. | |
| 2005/0255317 A1 * | 11/2005 | Bavaro | A61B 90/39 428/375 |
| 2006/0015039 A1 * | 1/2006 | Cassidy | A61M 25/09 600/585 |
| 2006/0149165 A1 * | 7/2006 | Kennedy, II | A61B 5/1076 600/585 |
| 2006/0161241 A1 * | 7/2006 | Barbut | A61F 2/856 623/1.15 |
| 2007/0055341 A1 * | 3/2007 | Edoga | A61F 2/07 623/1.11 |
| 2007/0129785 A1 * | 6/2007 | Vreeman | A61F 2/915 623/1.11 |
| 2007/0249964 A1 * | 10/2007 | Richardson | A61L 31/10 600/585 |
| 2008/0146967 A1 * | 6/2008 | Richardson | A61L 31/18 600/585 |
| 2009/0162531 A1 * | 6/2009 | Nesbitt | A61L 29/085 427/2.12 |
| 2009/0234247 A1 | 9/2009 | Iwamori et al. | |
| 2010/0056958 A1 * | 3/2010 | Ravi | A61B 5/1076 600/587 |
| 2010/0217370 A1 * | 8/2010 | Scheuermann | A61L 31/022 623/1.11 |
| 2010/0305476 A1 * | 12/2010 | Thornton | A61B 5/0002 600/585 |
| 2011/0301501 A1 * | 12/2011 | Tsunezumi | A61M 25/09 600/585 |
| 2012/0271409 A1 * | 10/2012 | Bruszewski | A61M 25/09 623/1.34 |
| 2014/0058251 A1 * | 2/2014 | Stigall | A61B 1/05 600/424 |
| 2014/0100484 A1 * | 4/2014 | Tsusaka | A61B 5/6885 600/587 |
| 2017/0021139 A1 * | 1/2017 | Bajema | A61M 25/104 |
| 2017/0050000 A1 * | 2/2017 | Randall | A61M 25/0108 |

FOREIGN PATENT DOCUMENTS

| | | | |
|---|---|---|---|
| EP | 2392376 | 12/2011 | |
| WO | WO 95/24237 | 9/1995 | |
| WO | WO 96/23441 | 8/1996 | |
| WO | WO 96/39077 | * 12/1996 | ............. A61B 5/107 |

* cited by examiner

ILIAC AORTIC MEASUREMENT

GUIDE WIRE FOR MEDICAL DEVICES, METHOD OF USING THE GUIDEWIRE, AND METHOD FOR FORMING A COVERING ON THE GUIDEWIRE

REFERENCE TO PENDING PRIOR PATENT APPLICATIONS

This patent application is a continuation-in-part of pending prior U.S. patent application Ser. No. 15/121,414, filed Aug. 25, 2016 by SYMEDRIX GmbH for GUIDE WIRE FOR MEDICAL DEVICES, which in turn is a 371 national stage application of International (PCT) Patent Application No. PCT/EP2015/053305, filed Feb. 17, 2015 by SYMEDRIX GmbH for GUIDE WIRE FOR MEDICAL DEVICES, which in turn claims benefit of German Patent Application No. DE 20 2014 100 863.2, filed Feb. 26, 2014.

The three (3) above-identified patent applications are hereby incorporated herein by reference.

FIELD OF THE INVENTION

The present invention relates to a guide wire for medical devices. a method of using the guide wire, and a method for forming a covering on the guidewire.

BACKGROUND OF THE INVENTION

Guide wires are used in particular in minimal invasive surgery and in endoscopy, to deliver medical devices such as catheters or stents over these guide wires into vessels and organs of the patient.

In order to be able to make an exact positioning of the guide wire possible, it is known to provide a marker at the distal end of the guide wire. This marker may, for example, be a ball of radiopaque material.

In addition, it is known to provide markings over the length of the guide wire. These markings are incorporated into a sheath of the guide wire or are applied onto the sheath. Such a guide wire is, for example, described in EP 1 208 868 A2. The markings herein are in particular helical color markings, which can be detected through an optical lens of an endoscope.

One disadvantage of these known guide wires is that during interventions and medical procedures in which the guide wire is to be used without usage of an endoscope, the detection of the markings is not possible. In addition, due to their helical arrangement, these markings are not suitable for providing the surgeon with an indication of a length or a distance in the body of a patient. Moreover, the manufacturing of these guide wires is cumbersome, since a separate application or integration of the markings in the sheath is necessary.

SUMMARY OF THE INVENTION

An objective of the present invention is thus to provide a solution, wherein a guide wire can be manufactured in a simple manner and nevertheless is suitable for measuring of lengths or distances in the body of the patient.

The invention is based on the finding that this object can be achieved by integrating a measuring scale into the guide wire, which consists of areas of a spiral, in particular of spiral areas with different radiopacity.

According to the invention, the object is thus achieved by a guide wire for medical devices, which has at least one marking. The guide wire is characterized in that the guide wire in its distal end has a spiral, which extends from the distal end of the guide wire in the proximal direction and which has at least two adjoining spiral sections as markings, wherein at least two of the spiral sections consist of different materials at least at their surface.

A guide wire according to the present invention refers to a medical guide wire, which can be used for introducing medical devices. At least at its distal end the guide wire has a spiral. Distal end in the sense of the present invention refers to the end or area, which is facing away from the surgeon during the insertion of the guide wire into the patient. Proximal end refers to the end or area which is opposite of the distal end and which is facing the surgeon and via which the surgeon generally actuates the guide wire, that means moves and positions the guide wire. In the distal end of the guide wire, the guide wire according to the invention has a spiral. The distal end can be formed by the spiral, in particular by the distal end of the spiral itself. It is, however, also possible that at the distal end of the spiral, and thus of the guide wire, a ball is provided which is affixed to the spiral, in particular welded thereto. According to the invention, the spiral extends from the distal end of the guide wire in proximal direction. Preferably, the spiral does not extend over the entire length of the guide wire but has a length which is smaller than ¼ of the overall length of the guide wire. The spiral is preferably attached to a wire of the guide wire, which wire is preferably formed by a solid wire. The spiral can be welded to the distal end of the wire.

According to the invention, the spiral has at least two spiral sections. The spiral sections are adjoining to each other, that means are adjacent to each other. Preferably, the spiral has several spiral sections. In the guide wire according to the invention, the spiral sections serve as markings. For this purpose, the individual spiral sections consist at their surface at least of different materials. Herein, in particular, the material of the surface of adjacent spiral sections differs. Spiral sections which are spaced from each other, which are separated by one or more different spiral sections, may according to the invention at least at their surface consist of the same material. The spiral sections, which have different materials at their surface, will hereinafter also be referred to as types of spiral sections. According to the invention at least two types of spiral sections are contained in the spiral. It is, however, also within the scope of the invention to provide three or more types of spiral sections in the spiral. Herein the spiral sections are each arranged such that the material of two spiral sections which are adjacent to each other is always different.

The base material of the individual spiral sections may be the same. In this embodiment, the spiral may be designed as a one-piece. In this case, the individual spiral sections merely differ by the material at their surfaces.

Since the guide wire according to the invention has at least two spiral sections, which at least at their surface consist of different materials and which serve as markings, a number of advantages can be achieved. Firstly, the guide wire can be manufactured in a simple manner since a separate manufacture of a sheath with markings is not necessary. Moreover, a scale is formed at the guide wire due to the markings which are provided at the guide wire itself and which is formed by the spiral sections and which allows for measuring of lengths or distances in the body of a patient. As the markings are provided at the distal end of the guide wire, they lie in the introduced state of the guide wire in the immediate vicinity to the vessels or organs which are to be measured and a measurement can thus be carried out reliably. In addition, the materials of adjoiningly arranged spiral sections can be chosen such that these have different properties and can thus be displayed to the surgeon differently, since at the spiral sections at least at their surfaces different materials are provided. By detecting the different spiral sections while knowing the length of each individual spiral section, the surgeon can measure a length or a distance within the patient, in particular in a vessel or organ in a simple manner. Finally, the round wire or flat wire, of which the spiral of the guide wire consists, is preferably wound such that the individual windings of the spiral each are in contact with each other. As in the spiral sections of such a spiral, at least at the surface a different material is provided than in adjacent spiral sections, a marking is formed, which lies essentially perpendicular to the longitudinal axis of the guide wire on the circumference of the guide wire. Therefore, the markings according to the invention in comparison to helically provided markings have the further advantage that these are suitable as a graduation or can form such a graduation.

According to a preferred embodiment, at least the surface of at least one of the at least two spiral sections consists of a material with lower transmissibility of radiation than the transmissibility of radiation of the material of at least one other of the at least two spiral sections.

If the spiral consists of only two spiral sections, the area at which surface the material has a lower transmissibility for radiation, is arranged spaced from the distal end of the spiral and, at the distal end of the spiral, a marking, for example, in the shape of a ball with also lower transmissibility for radiation is provided. Between the ball and the spiral section with lower transmissibility for radiation, a spiral section with higher transmissibility for radiation is provided. In this case the distance between the distal end and the spiral section with lower transmissibility for radiation can serve as a scale for the surgeon during the measurement of a distance.

Preferably, more than two spiral sections are provided. With this embodiment, it is preferred that at least the material at the surface of adjacent spiral sections is different from the other. In particular, in this embodiment, a spiral section having a higher transmissibility for radiation is adjacent to one or two spiral sections having lower transmissibility for radiation and one spiral section with lower transmissibility for radiation is adjacent to one or two spiral sections having lower transmissibility for radiation.

Since at least at the surfaces of the spiral sections materials with different transmissibilities for radiation are provided, the different spiral sections can easily be distinguished from each other by a surgeon during the radiation.

According to a preferred embodiment, at least one of the spiral sections has a coating. The coating covers herein preferably at least the outer side of the spiral section, that is the outer surface of this spiral section. Preferably, a spiral section which has a coating is adjacent to an uncoated spiral section or to a spiral section having a different coating. The base material of the different spiral sections may be the same.

Since at least one of the spiral sections has a coating, which preferably has properties, which differ from the properties of the base material and/or from the material of the surface of the adjacent spiral sections, it is not necessary to produce one or several spiral sections entirely from a material with the desired properties, in particular low transmissibility for radiation. Since these materials are generally expensive, the provision of a coating is advantageous. In addition, when providing a coating, the base material of the spiral section can be chosen depending on other criteria, in particular depending on its flexibility and elasticity. Finally, in this embodiment, the spiral may be made of one piece and the different spiral sections can be formed merely by the coating or omission of coating.

According to a preferred embodiment, the coating, which is provided in at least one spiral section, is formed by vaporization. Vaporization has the advantage that the thickness of the coating can be set equally. In addition, the windings of the spiral, which generally are wound from a round wire or flat wire, can reliably be coated. Finally, during vaporization only a part of the spiral can be coated selectively and thereby a spiral section with appropriate surface properties can be generated. For this purpose, the sections of the spiral where no coating is to be generated can be covered, in particular, shielded by a mask.

According to a preferred embodiment, at least the surface of at least one spiral section consists of a radiopaque material, in particular, of gold, wolfram and/or barium sulfate. Further materials, which can be used as a surface of the spiral section(s) with radiopaque material, for example, are tantalum, platinum, niobium, palladium, silver or iridium. It is also within the scope of the invention, that the spiral in one or several sections completely consists of such radiopaque material.

According to a preferred embodiment, the spiral sections are separate parts, which are connected to each other at the ends which are facing each other, in particular welded. After having been connected to each other, the spiral parts form the spiral. Herein the distal end of one spiral part is connected to the proximal end of the next adjacent spiral part.

These embodiments have a number of advantages. On the one hand, the length of the individual spiral parts can be reliably set. For this purpose, from two or more raw spirals, which consist of different materials, a piece on the desired length can each be separated, in particular cut off, and the pieces of the different raw spirals are then connected to each other to form the spiral. In addition, this embodiment is of specific advantage for spiral sections which are to have a coating, since the coating can be brought onto the raw spiral on its entire length and a covering (e.g., masking) of sections of the spiral is not necessary anymore. Furthermore, also spiral sections of different lengths can be manufactured in a simple manner with this embodiment.

The separate spiral parts, which in particular have been cut off from a raw spiral, are connected to each other according to the invention, to thereby form the spiral of the guide wire. The connecting is preferably carried out by welding the spiral parts to each other, wherein the proximal end of a spiral part is welded to the distal end of a further spiral part. Connecting techniques such as spot-welding, laser welding and the like can be used. When connecting the spiral parts to form the spiral, in particular only the ends of the round wires or flat wires, which have formed by the separating from the raw spiral, are connected to each other. The windings of adjacent spiral parts which are in contact with each other, in contrast are preferably not welded to each other. Thereby the elasticity and flexibility of the spiral of the guide wire can still be ensured.

According to a preferred embodiment, at least two spiral sections form a scale. For this purpose, preferably at least three spiral parts are provided adjacent to each other. Since the scale is formed at the guide wire itself, the usage of a separate measuring catheter or the like is not necessary.

It is particularly preferable that the spiral sections have a predetermined length and predetermined distances in the scale. By this layout of the spiral sections, the surgeon, who is aware of the length and the distances, can immediately read a length or a distance, for example, from an x-ray image. According to one embodiment, for example twenty spiral sections are provided in the scale, wherein these comprise two different types of spiral sections, which are arranged in an alternating manner. The length of the individual spiral sections can be for example 1 cm. It is, however, also within the scope of the invention to produce shorter spiral sections, for example with a length in the range of 0.5 cm to 10 cm.

The spiral sections, according to an embodiment may, however, also have different lengths. For example, it is possible, that the length of the spiral sections continually increases from the distal end of the spiral to the proximal end of the spiral. It is, for example, also within the scope of the invention that the spiral has two different types of spiral sections and one type of the spiral sections has a greater length than the other type, wherein the two types of the spiral sections preferably lie alternatingly in the spiral of the guide wire. In any case, a scaling at the spiral of the guide wire can also be established with the spiral sections, which allow a measuring of lengths or distances for the surgeon.

According to a further embodiment, in addition to the different spiral sections as markings in the distal end of the guide wire, at least one indication can be provided at the proximal end of the guide wire, which corresponds to the at least one marking in the distal end, in particular to a spiral section, of the guide wire. The indication can comprise lines, color markings and/or numbers. The indication is preferably provided at the proximal end of the guide wire. More particularly, the indication is preferably provided in the area of the guide wire, which during the intervention or medical procedure (i.e., when a portion of the guide wire is inside of the patient) remains outside of the body of the patient and is thus visible for the surgeon. By means of this indication on the proximal end of the guide wire (which can also be referred to as a reference marking or reference markings), the measurement, which the surgeon can carry out with the markings in the distal end of the guide wire, can be checked or verified, respectively. Providing a reference marking is, however, not mandatorily necessary for the guide wire according to the invention.

According to a preferred embodiment, the guide wire comprises a wire having a wire core at its distal end and a wire shaft at its proximal end. The wire core comprises, at least at the distal end, at least a part of the spiral. The spiral is preferably connected, in particular welded, to the wire at the proximal end of the wire core. The wire core preferably represents a wire core which is tapered in the distal direction, that means which is conically shaped. The wire core is preferably designed as one piece with the wire shaft (i.e., the proximal end of the wire). The wire core can in particular be manufactured by grinding the wire. Subsequently, the spiral is put onto the wire core and is welded to the distal end of the wire shaft. At its proximal end, the spiral thus has an outer diameter, which corresponds to the outer diameter of the wire shaft. In the distal direction, the diameter of the spiral can be unchanging or can decrease.

In one preferred form of the invention, there is provided a guide wire for medical devices, which has at least one marking, characterized in that the guide wire in its distal end has a spiral, which extends from the distal end of the guide wire in a proximal direction and which has at least two adjoining spiral sections as markings, which at least at their surface consist of different materials.

In another preferred form of the invention, there is provided a method for measuring a distance in a body vessel and introducing an implant into the body vessel, the method comprising providing a guide wire, wherein the guide wire comprises a proximal end and a distal end, wherein the distal end comprises a spiral which has at least two adjoining spiral sections as markings, wherein at least a surface of one spiral section comprises a first material and at least a surface of the second spiral section comprises a second material, and further wherein the first material is different than the second material; inserting the guide wire into the body vessel; measuring the distance in the body vessel using the markings on the guide wire; and delivering the implant over the guide wire to the body vessel.

In another preferred form of the invention, there is provided a method for forming a covering on a guide wire, wherein the guide wire comprises a proximal end and a distal end, wherein the distal end comprises a spiral which has at least two adjoining spiral sections as markings, wherein at least a surface of one spiral section comprises a first material and at least a surface of the second spiral section comprises a second material, and further wherein the first material is different than the second material, the method comprising: advancing a sleeve over at least the spiral sections of the guide wire; and shrinking the sleeve over at least the spiral sections of the guide wire, whereby to form a covering on the guide wire.

In another preferred form of the invention, there is provided a guide wire for measuring a distance in a body vessel and introducing an implant into the body vessel, wherein the guide wire comprises at least one marking, characterized in that the guide wire in its distal area has a spiral, which extends from the distal end of the guide wire in a proximal direction and which has at least two adjoining spiral sections as markings, which at least at their surface consist of different materials.

In another preferred form of the invention, there is provided a guide wire for measuring a distance in a body vessel and introducing an implant into the body vessel, the guide wire comprising:
  a proximal end and a distal end, wherein the distal end comprises a spiral which has at least two adjoining spiral sections as markings, wherein at least a surface of one spiral section comprises a first material and at least a surface of the second spiral section comprises a second material, and further wherein the first material is different than the second material; and
  a covering, wherein the covering is formed by advancing a sleeve over at least the spiral sections of the guide wire and shrinking the sleeve over at least the spiral sections of the guide wire.

In another preferred form of the invention, there is provided a method for treating an abdominal aortic aneurysm (AAA), the method comprising:
  inserting a first guide wire having at least one marking into the aorta and positioning the first guide wire adjacent to the aneurysm;
  measuring a first distance within the aorta using the at least one marking on the first guide wire;
  selecting a first implant to be deployed in the aorta based on the first measured distance;
  delivering the first implant over the first guide wire to the aorta and deploying the first implant at the aneurysm;
  inserting a second guide wire having at least one marking into the aorta and positioning the second guide wire adjacent to the aneurysm;
  measuring a second distance within the aorta using the at least one marking on the second guide wire;
  selecting a second implant to be deployed in the aorta based on the second measured distance;

delivering the second implant over the second guide wire to the aorta and connecting the second implant to the first implant;

measuring a third distance within the aorta using the at least one marking on the first guide wire;

selecting a third implant to be deployed in the aorta based on the third measured distance;

delivering the third implant over the first guide wire to the aorta and connecting the third implant to the first implant.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The Novel Guide Wire of the Present Invention

Figure 1:
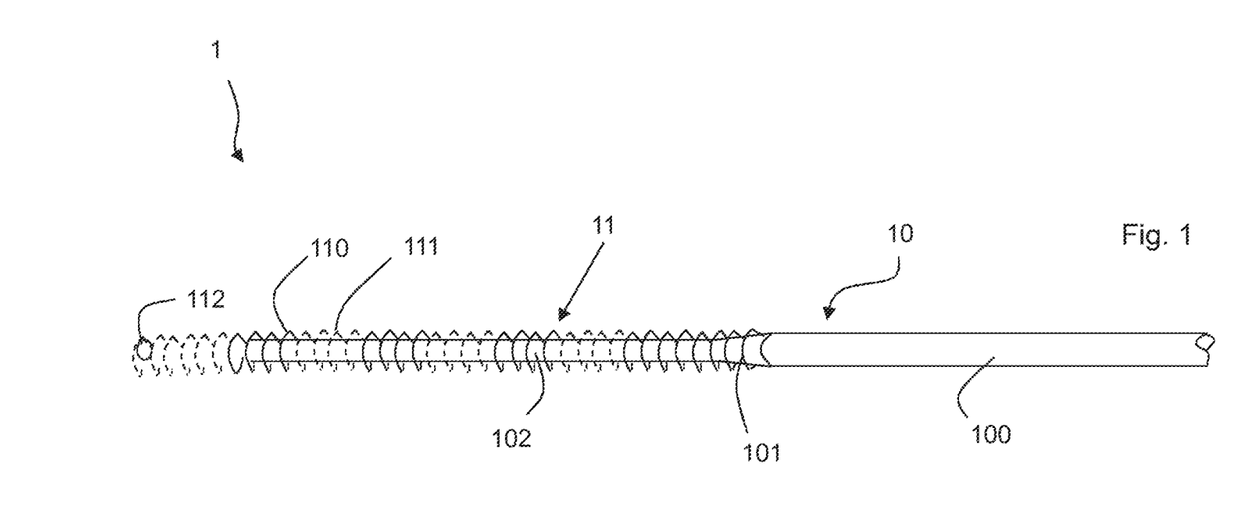
FIG. 1: shows a schematic depiction of an embodiment of the inventive guide wire.

In FIG. 1, an embodiment of the guide wire 1 according to the invention is shown. The guide wire consists of a wire 10 and a spiral 11. The wire 10 has a wire shaft 100 in its proximal end. In the distal end, the wire 10 is formed by a wire core 102. The wire core 102 has a smaller diameter than the wire shaft 100. Between the wire shaft 100 and the wire core 102 a transition area 101 is formed at the wire 10. In the depicted embodiment the transition area 101 is a conical area, over which the diameter of the wire 10 decreases from the wire shaft 100 to the wire core 102.

In the distal end the guide wire 1 is formed at least at its outside by the spiral 11. The proximal end of the spiral 11 is connected, in particular welded, at the transition area 101 with the wire 10. It is, however, also possible to attach, in particular to weld, the spiral 11 at the distal end of the wire shaft 100. Therein, the transition area 101 is received in the spiral 11. In the depicted embodiment, a ball 112 is welded to the distal end of the spiral 11. It is, however, also possible to design the guide wire 1 without a ball. The length of the spiral 11 may be larger than the length of the wire core 102. Thereby, the distal end of the guide wire 1 is exclusively formed by the distal end of the spiral 11 without wire core 102 extending through the spiral. The distal end of the spiral 11 designed, as shown in the figures, is straight. It is, however, also within the scope of the invention to design the distal end of the spiral 11 to be curved or bent. By way of example but not limitation, the distal end of the spiral could be curved by 180°.

Over the length of the spiral 11, spiral sections 110, 111 are distributed. Spiral sections 110 can, for example, be made of stainless steel, nitinol or a different material which is suitable for medical technology. The spiral sections 111, to the contrary, may, for example, be made of the same material as the spiral sections 110, but may be coated, in particular vaporized, at the surface with a radiopaque material, such as wolfram, tantalum, gold, platinum, niobium, palladium, silver or iridium.

According to an alternative embodiment, the spiral 11 is designed as one-piece and the spiral sections 110, 111 are only generated by coating of the parts 111. Alternatively and preferably, it is, however, also possible, that the spiral sections 110, 111 are separate spiral parts, which are connected together (e.g., welded) to form the spiral 11. When the spiral sections are separate spiral parts connected to one another, spiral sections 111 can, for example, also be entirely formed from a different material than the spiral sections 110. By way of example but not limitation, spiral sections 111 may be formed of wolfram, gold or a different radiopaque material. In any case, however, the material of which the spiral sections 111 consist also has an elasticity which allows for the introduction of the spiral 11 in a vessel or an organ of the patient.

The invention is not limited to only two different types of spiral sections 110, 111 being provided. It is rather also within the scope of the invention, that the spiral has more than two different types of spiral sections. Herein, the different types of spiral sections differ preferably by their transmissibility for radiation at least at their surface. Thereby, the different types of spiral sections appear differently, for example, on an x-ray image and are thus easy to distinguish for the surgeon.

The spiral sections 110, 111 are arranged over the length of the spiral 11 in predetermined distances and each have a predetermined length.

Figure 2:
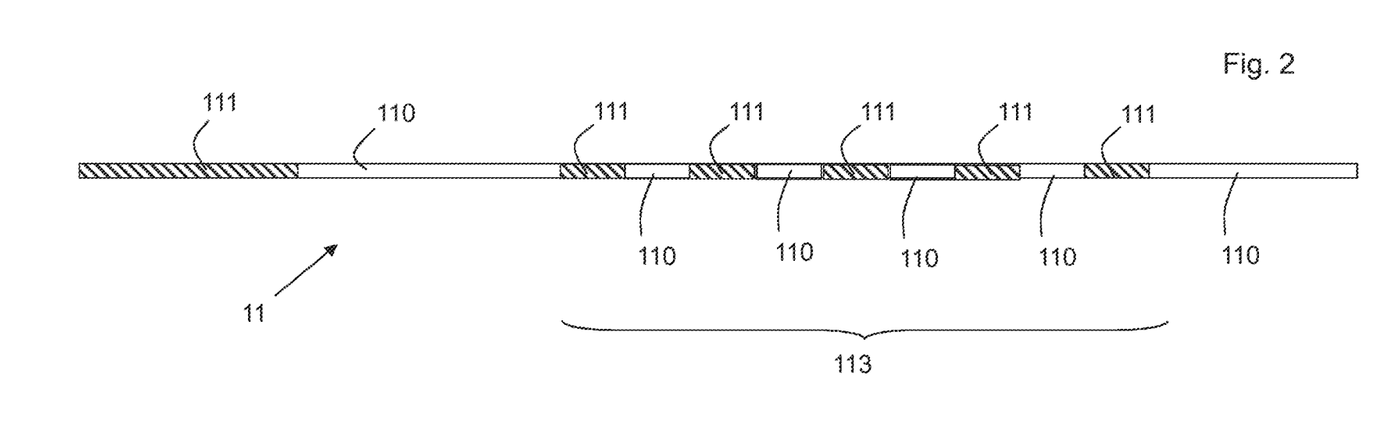
FIG. 2: shows a schematic depiction of an embodiment of the distribution of spiral sections of an embodiment of the spiral of the guide wire according to the present invention.

In FIG. 2 a schematic depiction of a possible distribution of the spiral sections 110, 111 for an embodiment of the spiral 11 of the guide wire 1 is shown. In this embodiment, at the distal end, a spiral section 111 with a higher radiopacity, for example, a stainless steel coated with gold or wolfram, is provided. In the proximal direction, a longer spiral section 110 adjoins spiral section 111, wherein the spiral section 110 can also, for example, consist of stainless steel. In the depicted embodiment, five spiral sections 111 of a smaller length follow, between which a spiral section 110 of also smaller length is provided, respectively. The length of the shorter spiral sections 110, 111 is preferably equal. More than the depicted five spiral sections 111 can be provided. Since the shorter spiral sections 110 and 111 are present alternatingly and each have the same length, a scale 113 is formed, which serves the surgeon for measuring distances and lengths. Since the material of the spiral sections 110, 111 in the scale 113 have a different radiopacity, the different spiral sections 110, 111 are easily detectable for the surgeon on an x-ray image.

Figure 3:
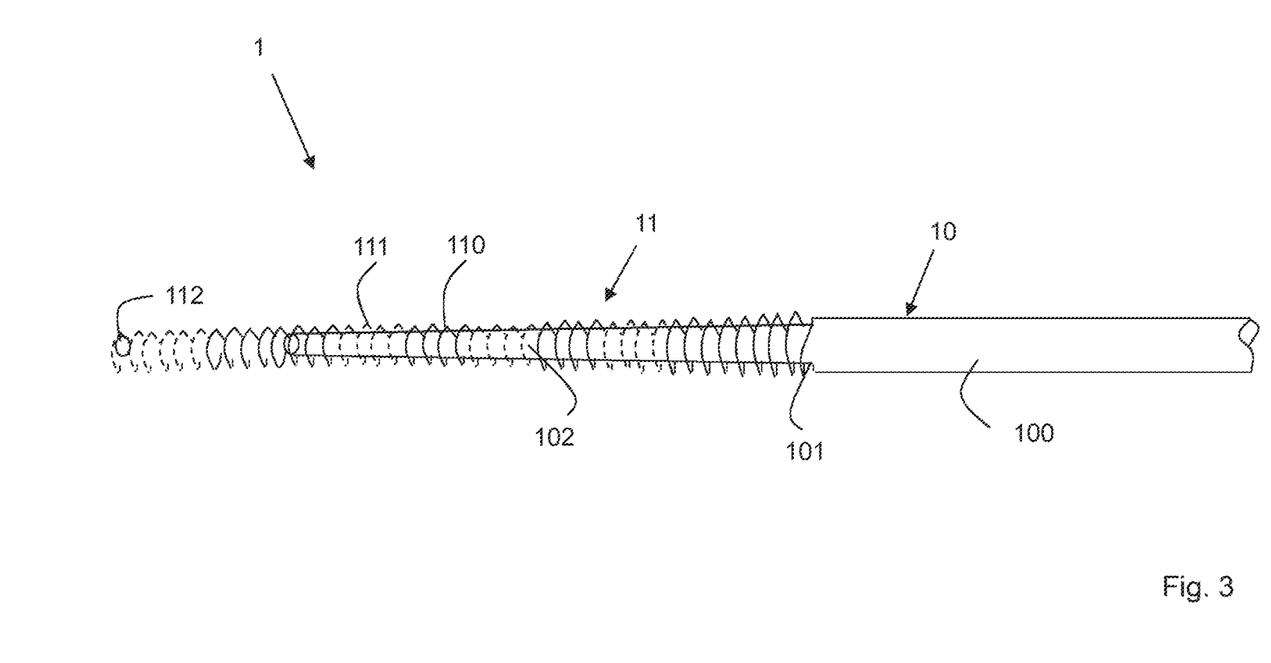
FIG. 3: shows a schematic depiction of a further embodiment of the guide wire according to the invention.

In FIG. 3, a further embodiment of the guide wire according to the invention is shown. This embodiment differs from the embodiment shown in FIG. 1 only in that the wire core 102 is designed conically (instead of straight) and thus tapers towards the distal end of the wire core. Also the spiral 11 is designed conically in this embodiment. In addition, in the embodiment according to FIG. 3, the transition area 101 is formed as a pitch or step, at which the diameter of the wire shaft 100 decreases to the diameter of the wire core 102 at the proximal end of the wire core 102. At this transition area 101 or step of wire 10, the proximal end of the spiral 11 is attached, in particular glued or welded. The further structure of the guide wire 1 and in particular of the spiral 11 corresponds to the embodiment shown in FIG. 1.

Figure 4:
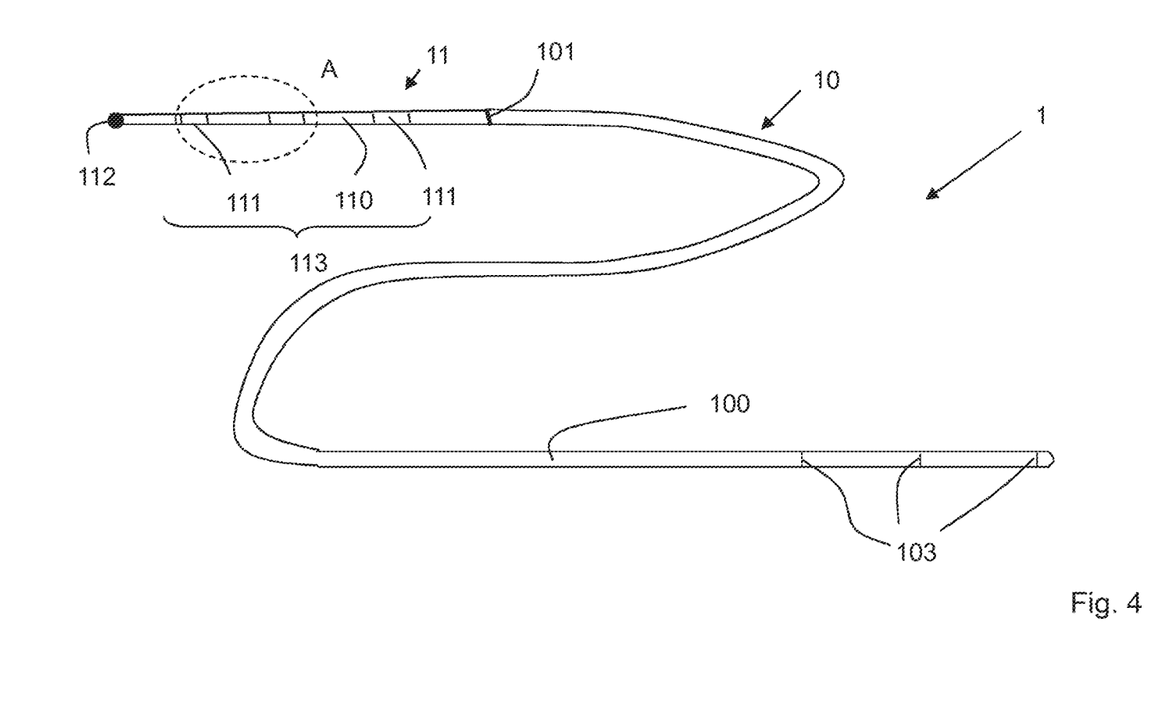
FIG. 4: shows a schematic depiction of a further embodiment of the guide wire according to the present invention.

In FIG. 4, a further embodiment of the guide wire 1 according to the invention is shown. The structure of the guide wire 1 corresponds to the structure of the embodiment according to either FIG. 1 or FIG. 3. In addition, in the embodiment according to FIG. 4, reference markings 103 are provided on the proximal end of the wire 10, the distance of which to each other correspond to the distances of the spiral sections 110, 111 in the scale 113.

The figures are not to scale. The guide wire 1 can for example have a length of 2.50 m and the length of the spiral can be 50 cm. The spiral sections 110, 111, in particular the spiral sections 110, 111 which form the scale 113, may for example each have a length in the range of 0.5 cm to 10 cm, preferably in the range of 0.5 cm to 1.5 cm. According to an embodiment, the length of the individual spiral sections 110, 111 in the scale are, for example, 1 cm each.

Figure 5:
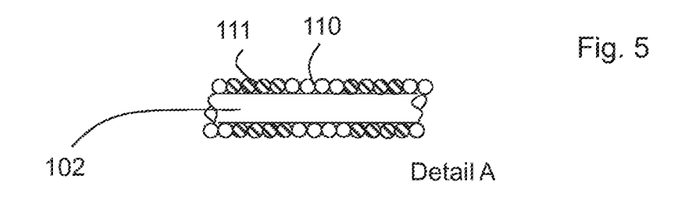
FIG. 5: shows a detailed view of the spiral sections of FIG. 4.

In FIG. 5, a detailed view of the area of the scale 113 of FIG. 4 is shown. As can be derived from this detailed view A in FIG. 5, the spiral sections 110 and 111, which have different surface properties, alternate in the scale 113. The spiral sections 110 and 111 each have the same length in the area of the scale 113 in the depicted embodiment.

The invention is not limited to the depicted embodiments. For example, more or less than the depicted spiral sections 110, 111 may be arranged in the scale 113. In addition, also further spiral sections, which have a surface property, in particular radiopacity, different to the spiral sections 110, 111 can be integrated in the scale 113.

Furthermore, for example, the lengths of the individual spiral sections 110, 111 in the scale 113 may increase in one direction. For example, spiral sections 110, 111 with a shorter length can be arranged in the distal area of the scale 113 and the length of the respective spiral sections 110, 111 can increase gradually in the proximal direction in the scale 113.

The present invention thus provides a solution, wherein a guide wire can be manufactured in a simple manner but nevertheless is suitable for measuring lengths or distances in the body of a patient. Therein, in particular, a measuring scale is integrated in the wire, which consists of parts of the spiral of the guide wire and in particular of spiral sections with different radiopacity.

Preferably, a spiral of the guide wire according to the invention is composed of at least two spiral parts. The spiral parts are preferably glued or welded to each other. The welding can preferably be carried out by means of a laser. According to a preferred embodiment, at least in the distal end of the guide wire, at least two, preferably at least three spiral parts, are attached to each other in an axial direction. Therein the spiral parts may each have the same length. According to a further embodiment, the length of the spiral parts increases in a proximal or a distal direction.

The present invention has a number of advantages. In particular, and as will be discussed in further detail below, it is possible with the present invention to conduct an intravascular measuring of vessels and/or organs and in particular to determine their length. In addition, for example, vessel distances can be determined. This is, for example, of importance for determining the length of a prosthesis or implant which is to be inserted into the vessel. Therein and in other steps, which necessitate the determination of the length of a vessel and/or organ and/or of a vessel distance, the usage of separate measuring catheters is no longer necessary when using the guide wire according to the invention. Instead the guide wire, via which the prosthesis or other medical device is guided, can simultaneously be used for measuring. Thereby the entire medical procedure is simplified and the duration of the medical procedure is shortened.

Finally, the manufacturing of the guide wire is simplified, as the spiral, at which the spiral sections are formed, can be manufactured beforehand and subsequently only has to be attached to the wire of the guide wire. Furthermore in an embodiment, wherein the spiral sections are formed by separate spiral parts, the length of the spiral parts can easily and reliably be established by cutting the separate spiral sections in the corresponding length off of a raw spiral.

A Method of Using the Novel Guide Wire of the Present Invention to Measure a Length or a Distance in a Body Vessel and/or to Introduce an Implant into the Body Vessel In one preferred form of the present invention, guide wire 1 may be used to measure a length or a distance in a body vessel of a patient, and/or to introduce an implant into the body vessel (or other body lumen) in order to treat a defect in the body vessel. More particularly, guide wire 1 can be used to measure the length of a lesion 200 in a body vessel, and to introduce an implant into the body vessel in order to treat the lesion in the body vessel. The method is preferably performed in accordance with the following steps.

Figure 6:
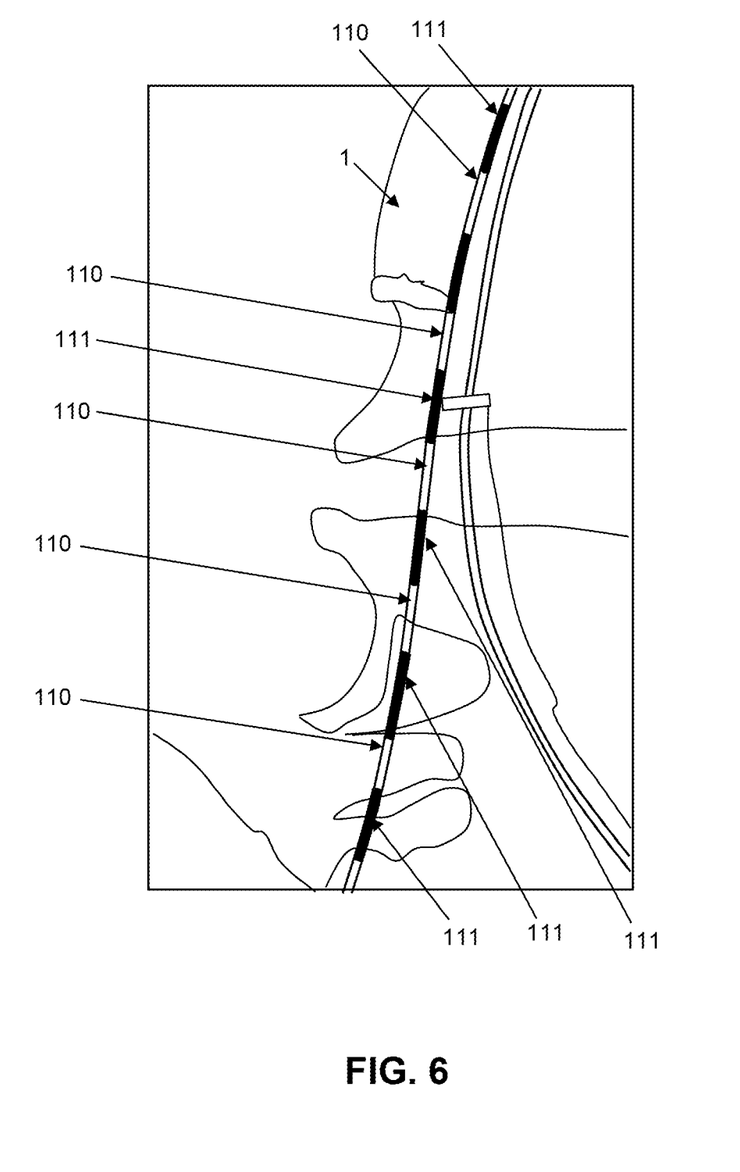
FIGS. 6 and 7 show the guide wire of the present invention in a body vessel.

Step 1. Guide wire 1 is introduced into a body vessel of a patient. See, for example, FIG. 6 which shows spiral sections 110 and 111 of guide wire 1 while guide wire 1 is positioned in a body vessel of a patient.

Figure 7:
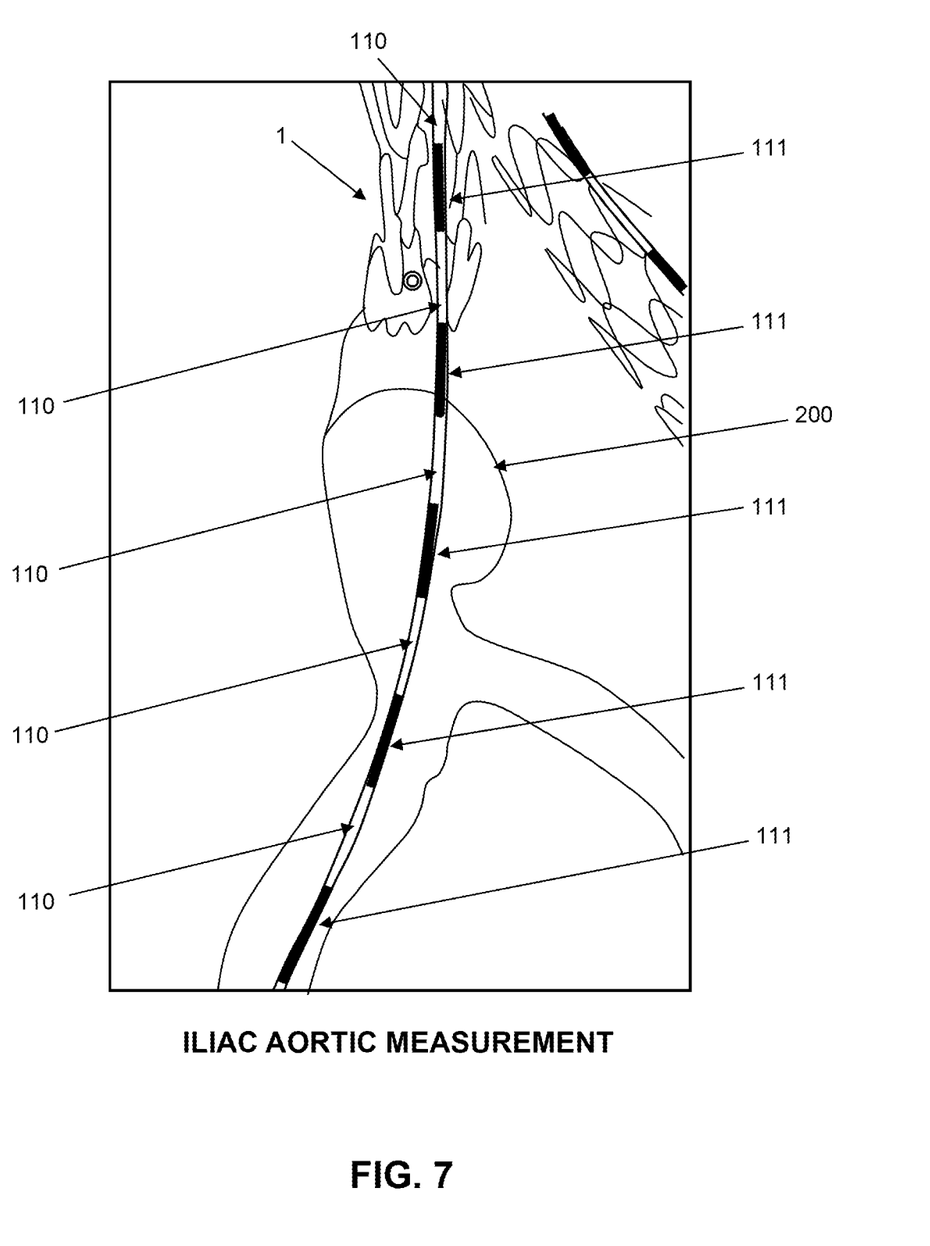

Step 2. A contrast agent is introduced into the vessel, thereby making the lesion 200 which is to be treated visible (FIG. 7).

Step 3. Spiral sections 110 and 111 of guide wire 1 (i.e., the marking area of guide wire 1) are positioned in the area of the lesion.

Step 4. The lesion and/or other distances within the body vessel are measured by counting the markings (i.e., spiral sections 110 and 111) on guide wire 1 in the area of the lesion.

Step 5. An implant having the desired length is selected for implanting in the body vessel.

Step 6. The implant is delivered to the area of the lesion in the body vessel. Preferably, a catheter is forwarded over the guide wire which has been positioned within the body lumen, and the implant is introduced through the catheter.

Step 7. The implant is placed within the body vessel according to the markings on the guide wire.

Step 8. The implant is deployed (e.g., expanded by withdrawing the catheter, or in other ways well known in the art), thereby securing the implant within the body vessel.

Optionally, after Step 7 the length of the implant may be verified by means of the scale 113 which is provided by the markings in the marking area of guide wire 1 (i.e., by spiral sections 110 and 111).

Further optionally, after Step 7, a distance from a determined point of the implant to a branching vessel of the body vessel may be measured, thereby avoiding blocking of the branching vessel by the implant.

As the length of each marking and the distance between the markings is preset, for example each being 1 cm, a length of a lesion or a distance within the body vessel can be determined by counting the respective markings on the guide wire.

In another preferred embodiment of the present invention, guide wire 1 can be used to provide an implant for the treatment of an abdominal aortic aneurysm (AAA). In this embodiment, the above-described method is used to position a main body of an implant in the main vessel of the aorta, i.e. between the branching off of the renal artery and the bifurcation of the femoral artery. Subsequently, guide wire 1 is used to measure the distance between the distal implant bifurcation and the internal artery. Thereby, the length of the first leg of the implant to be used and inserted into the external artery can be determined. The distance is determined again by counting the markings on guide wire 1 within this distance. The first leg of the implant is then advanced via guide wire 1 and is positioned in the external artery by using the markings on guide wire 1. After deployment of the first leg in the external artery, the required length of the second leg of the implant may be measured and the second leg of the implant may be inserted via the other external artery.

FIGS. 8-14 illustrate schematic details of using the guide wire of the present invention to measure a length or a distance in a body vessel and to introduce an implant into a body vessel in order to treat a defect in the body vessel.

Figure 8:
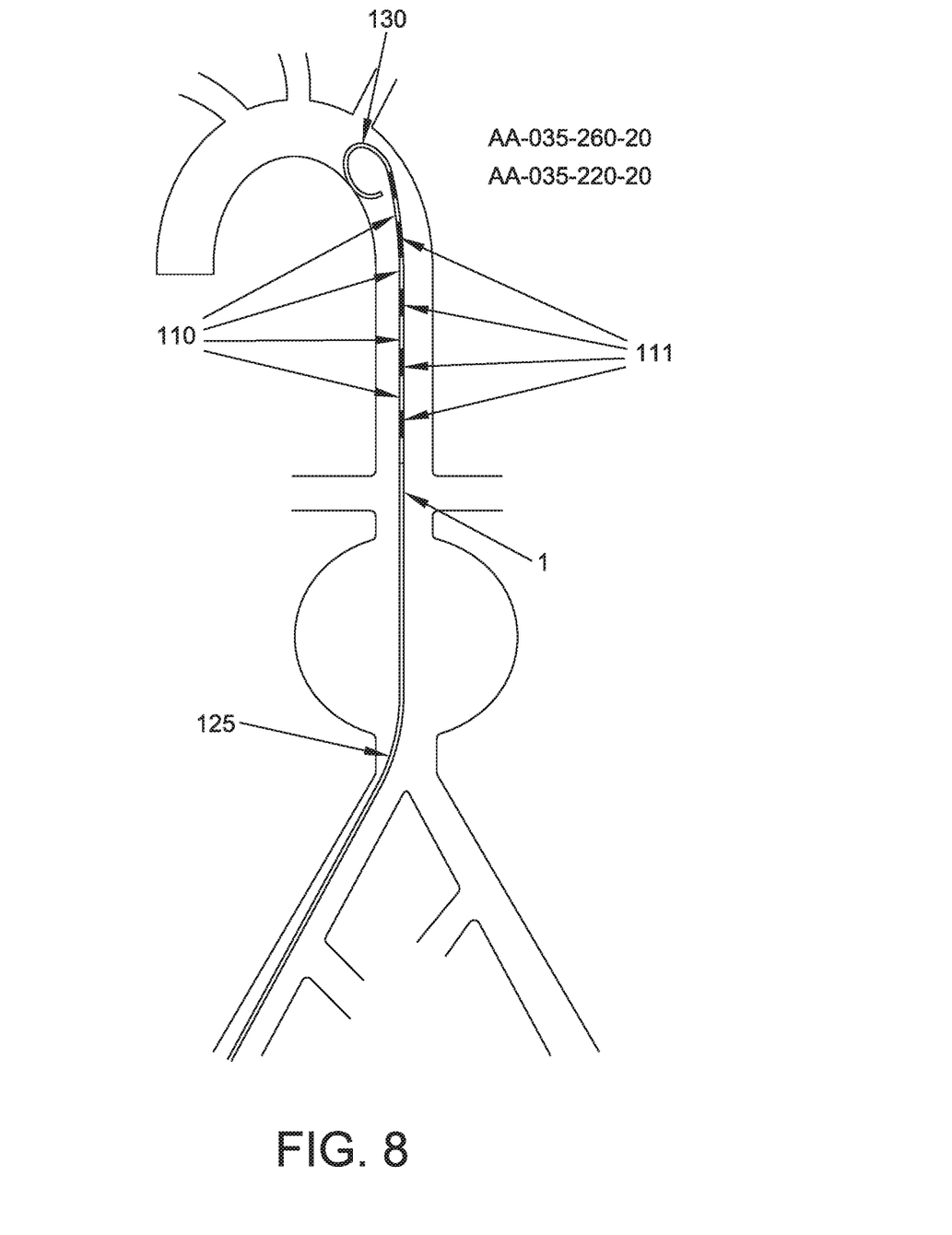
FIG. 8 is a schematic view of a guide wire of the present invention inserted into an aorta.

FIG. 8 schematically shows guide wire 1 inserted into the aorta. In this embodiment, proximal section 125 of guide wire 1 (i.e., the portion of the guide wire without the spiral sections 110 and 111) is a stiff section, which may have a length of, for example, 225 cm. The diameter of the proximal portion of the guide wire may be, for example, 0.89 mm. The distal section of the guide wire (i.e., the portion of the guide wire with spiral sections 110 and 111 is also a stiff portion (but less stiff than proximal section 125), which may have a length of, for example, 20 cm. The wire core 102 in the distal section of the guide wire may have a diameter of 0.6 mm. The spiral sections 110 and 111, i.e., the spiral parts which form the marking area or scale area of guide wire 1, are arranged on wire core 102. The distal tip portion 130 of guide wire 1 is a flexible portion which may have a length of, for example, 15 cm. Distal tip portion 130 may have no wire core or the wire core may be a conical wire core having a diameter which decreases from 0.6 mm to 0.18 mm. The overall length of the guide wire may be for example 220 mm to 260 mm.

Figure 9:
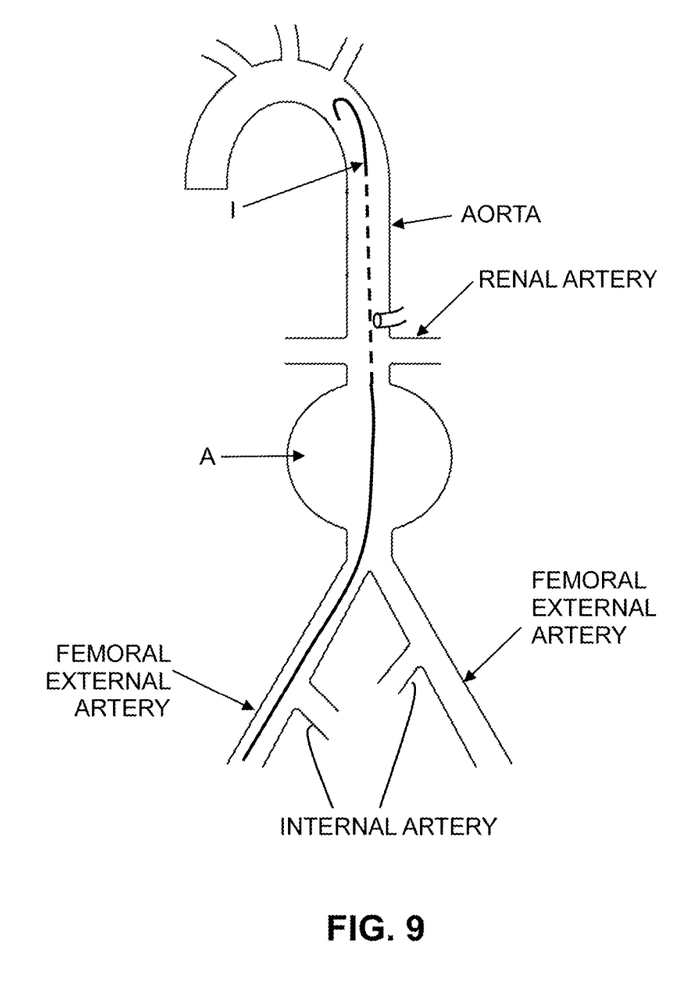
FIGS. 9-14 are schematic views of a method of treating an abdominal aortic aneurysm (AAA) using the guide wire of the present invention.
Figure 10:
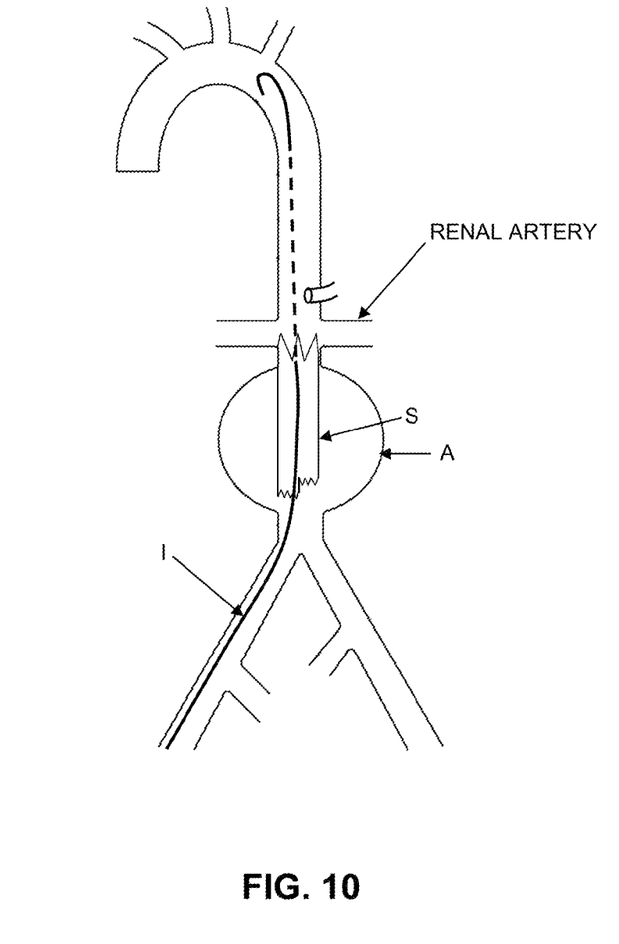

In FIGS. 9 through 14, the process of treating an abdominal aortic aneurysm (AAA) with a stent is schematically shown. In FIG. 9, it is shown that guide wire 1 is inserted into the aorta. From the position of FIG. 9, the guide wire is pulled back (i.e., moved proximally) until the marking area is within the area of the lesion, which in this case is an aneurysm A. By counting the markings which lay between the branching off of the renal artery and the bifurcation of the femoral artery, the distance between these vessels can be determined. In particular, each marking and each distance between markings may be 1 cm. The surgeon can thus determine the length of the main body of the implant (e.g., a stent graft) which should be implanted without blocking the renal artery or femoral artery. The selected main body of a stent S is then introduced into the vessel via guide wire 1 and is deployed as shown in FIG. 10.

Figure 11:
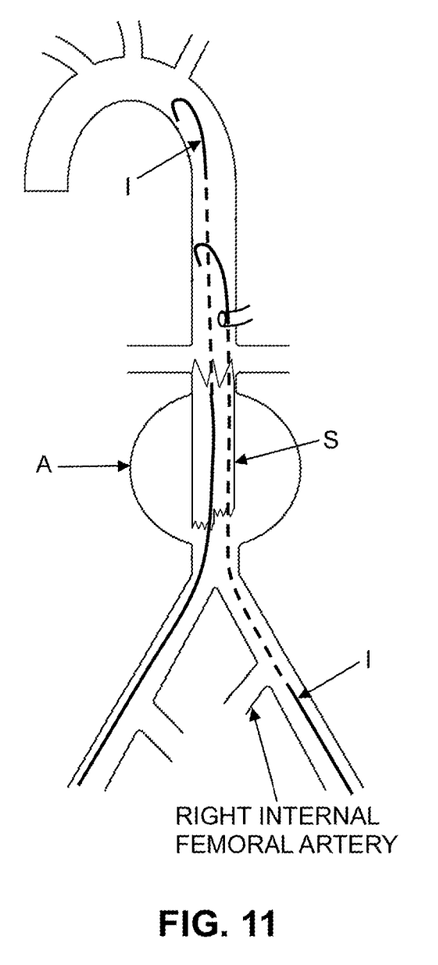
Figure 12:
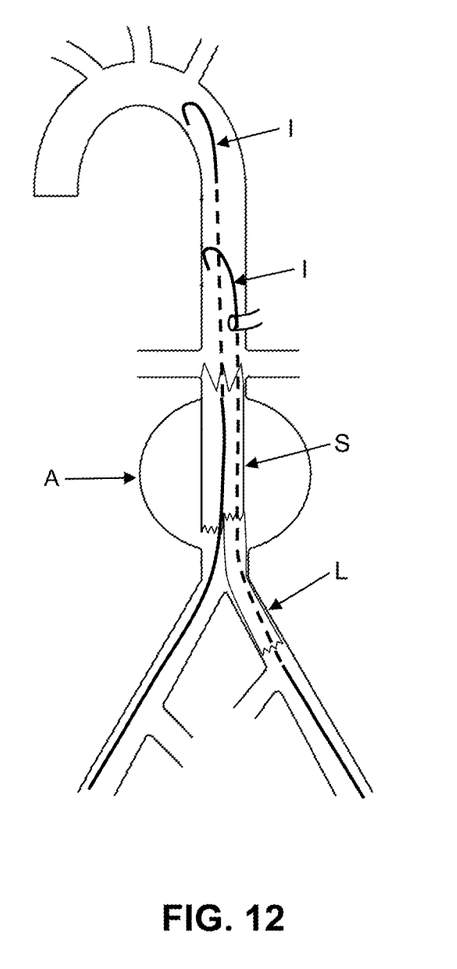

Next, and looking now at FIG. 11, a second guide wire 1 is introduced via the second femoral external artery and advanced into the contralateral limb of the main body of stent S. The guide wire is advanced to a position, where the marking area of the guide wire is within the main body of stent S and extends at least to the right internal femoral artery. By counting the markings and distances between the markings which lay between the bifurcation of the main body of stent S and the internal femoral artery, the length of the leg or limb that has to be used can be determined. The selected leg L of the stent is then introduced into the vessel and advanced to connect with the main body of the stent S. For positioning and deploying of the leg L, guide wire 1 may be advanced from the position shown in FIG. 12 in a proximal direction, so that the proximal section 125 of the guide wire 1 (i.e., the very stiff section shown in FIG. 8) of the guide wire is within the area of the contralateral limb to support the implementing of the leg L.

Figure 13:
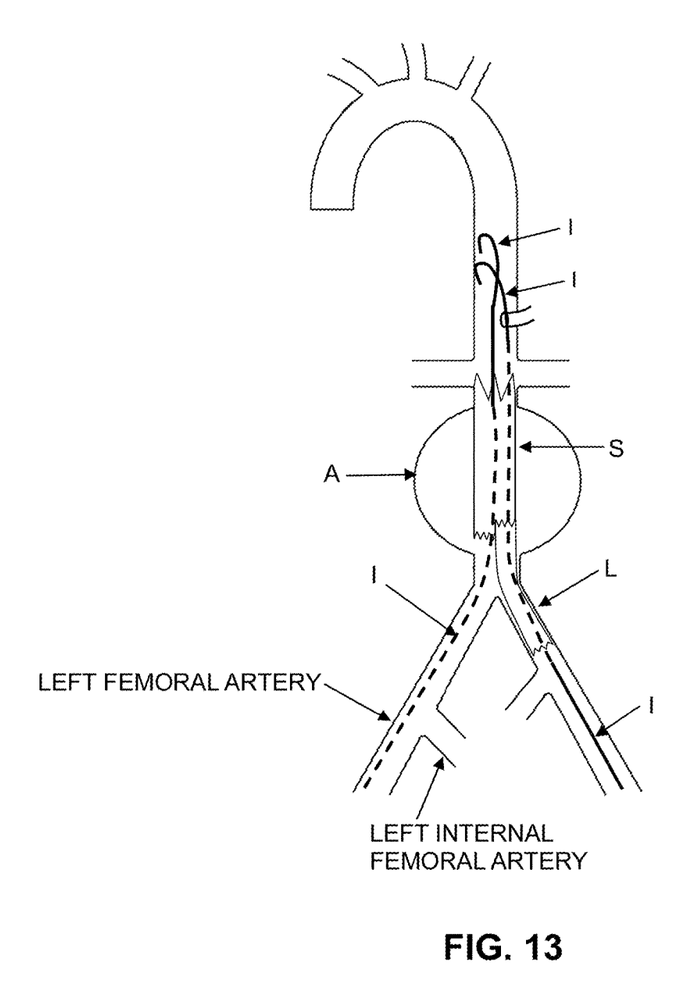
Figure 14:
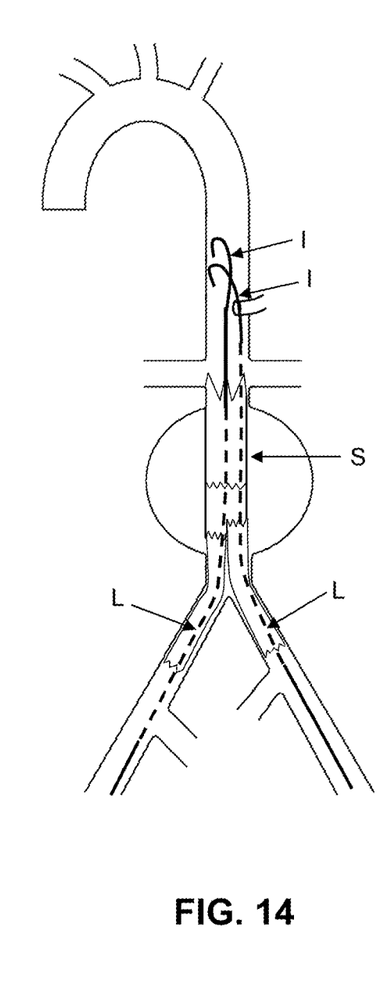

Looking next at FIG. 13, the first guide wire 1 which had been used to introduce the main body of the stent is pulled proximally so that the marking area lies within the main body of the stent and extends proximally to the left internal femoral artery. Thereby, the distance between the bifurcation of the main body of the stent and the internal artery can be measured by counting the markings in that distance. A leg L having the suitable length is then selected and inserted into the left femoral artery via the first guide wire 1. For deploying the second leg L, the first guide wire may be advanced distally, so that the stiff area of the guide wire (i.e., the area with spiral sections 110 and 111) is in the area of the ipsilateral limb of the stent. After deploying the second leg of the stent, both guide wires may be removed or may be used for guiding further treatment devices through the body vessel. FIG. 14 shows the stent in the final implanted position with the first and second guide wires still positioned in the patient.

It should be noted that the guide wire of the present invention can also be used to measure distances or lengths within other body vessels or body lumens of a patient which need to be treated, and it is not intended to limit the protection of the present invention to the treatment of an AAA.

When the guide wire of the present invention is used to measure a length or a distance in a body vessel of a patient and/or to introduce an implant into a body vessel of a patient, one or more of the following steps can also be performed before the guide wire is inserted:
  puncturing the tissue of the patient with a puncture needle,
  inserting a soft wire for probing the body vessel,
  removing of the puncture needle, and
  inserting an introducer sheath into a body vessel.

When an introducer sheath is first inserted into the body vessel, the guide wire is preferably inserted into the introducer sheath in order to introduce the guide wire into the body vessel.

After deploying the implant (or implants) in the body vessel, the introducer sheath and the guide wire will be removed and the puncture site will be closed in ways well known in the art.

The term implant as referred to in the foregoing discussion may include a stent, an implant or any other type of device which may be used to treat a lesion of a body vessel.

The term lesion as referred to in the foregoing discussion may refer to any one from the group consisting of stenosis, aneurysm, rupture and/or dissection, or any other defect in a body vessel or body lumen.

The measuring which is performed by means of counting the markings of the guide wire in the body vessel may be the measuring of the length of the lesion and/or measuring other distances within the vessel such as, for example, measuring a distance between two portions of a body vessel, measuring distances between vessels branching off of a main body vessel and/or measuring the distance of a point of an implant in the body vessel to a further vessel branching off of the main vessel. Hence, the length of the distance between the position of an implant and a branch vessel can be measured.

The main advantages of the method of the present invention are that the length is measured within the body vessel and not via a calibrated x-ray apparatus, which normally determines the length based on software to compensate for the difference between the actual length and the length shown in the X-ray pictures. The use of the guide wire with markings in the method is thus an intraluminal measurement, wherein the markings serve as a scale. The required length of an implant to be inserted into the body vessel can be determined precisely and any blocking of a branching off vessel or an insufficient covering of a lesion can be avoided.

A Covering for the Novel Guide Wire of the Present Invention

Figure 15:
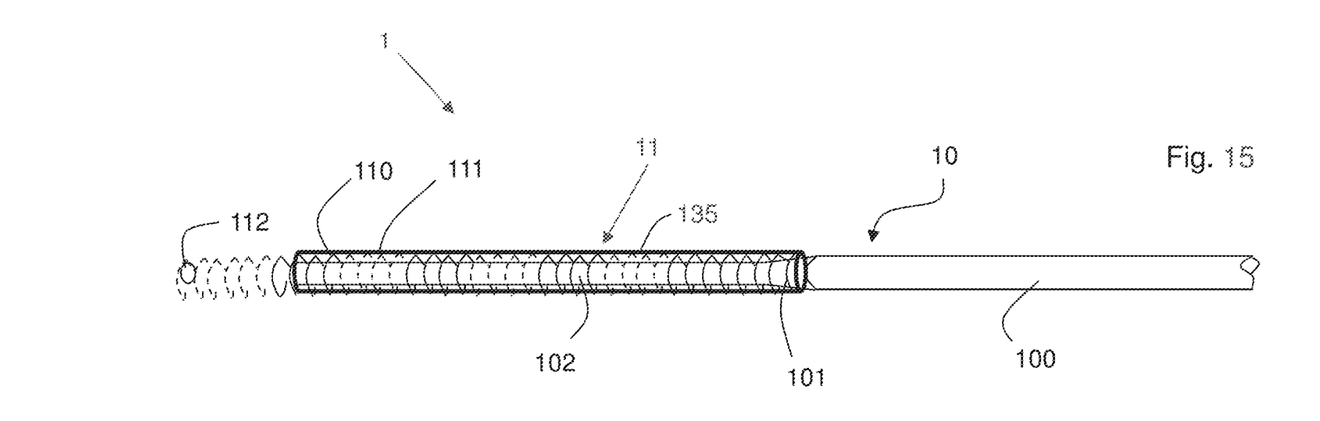
FIGS. 15-17 are schematic views of the guide wire of the present invention with a covering formed by shrink sleeving.
Figure 16:
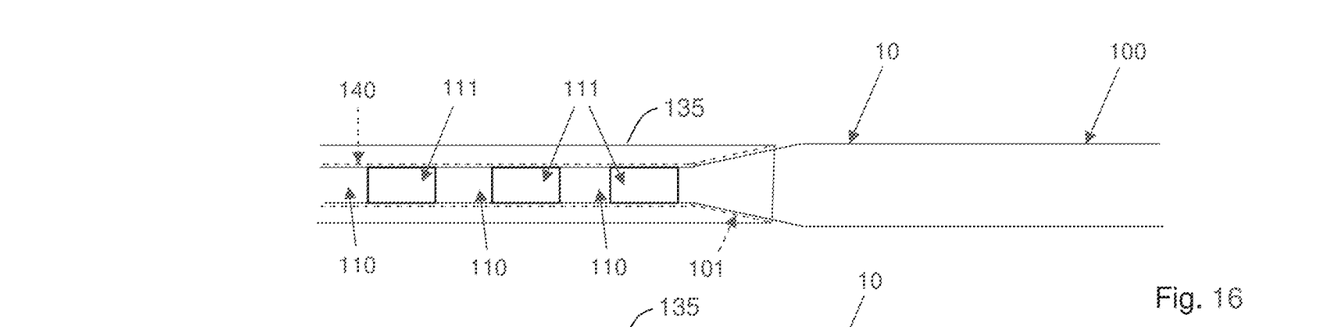
Figure 17:
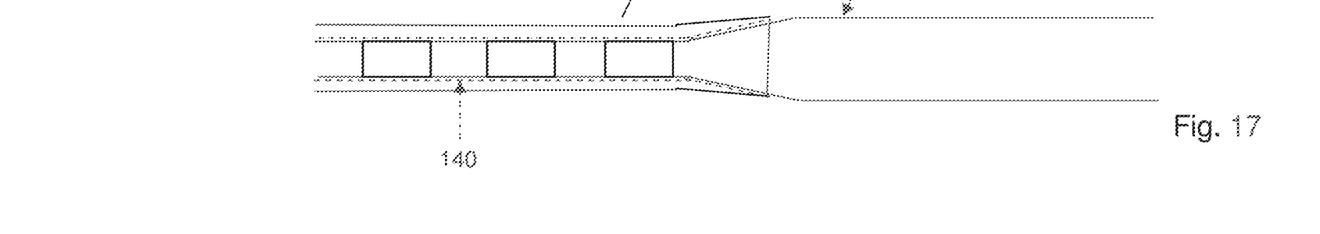

In another form of the present invention, and looking now at FIGS. 15-17, a covering 135 is provided on at least a portion of the surface of the guide wire in order to improve the surface properties of the guide wire. More particularly, a covering 135 is provided in the area of the markings on guide wire 1 (i.e., spiral sections 110 and 111 of guide wire 1). The covering is applied by using a shrink sleeving (which is also referred to as a shrinking tube), preferably made of polytetrafluoroethylene (PTFE). The shrink sleeving is advanced onto the guide wire from the distal end and is pushed over spiral sections 110 and 111 to the transition area 101 between wire core 102 and wire shaft 100 of the wire 10, which transition area is preferably a conical area, as shown in FIG. 1. After advancing the shrink sleeving over the guide wire, the shrink sleeving is heated, for example, by means of hot air applied through nozzles. The shrink sleeving may be heated up to, for example, 400-600° C. Heating the shrink sleeving causes the shrink sleeving to shrink, i.e. the diameter of the shrink sleeving is decreased so that the shrink sleeving securely rests on the guide wire, as is shown by dotted line 140 in FIGS. 16 and 17, thereby creating covering 135. It is important to note that the wall thickness of the shrink sleeveing (or shrinking tube) may decrease in the transition area 101 of the guide wire, as can be seen in FIG. 17.

The length of the shrink sleeving is preferably selected to be such that at least the area of the markings, in particular the welded spiral sections 110 and 111, is covered. In one form of the present invention, the shrink sleeving extends from the distal end of the wire core 102 (or just proximal to the distal end of the wire core 102) proximally to transition area 101. In other words, the shrink sleeving extends from the proximal end of the flexible end section of the guide wire 1. Thereby the flexibility of the distal end of the guide wire is not impaired by the shrinking tube.

It is preferable that the shrink sleeving is applied to spiral sections 110, 111 after the spiral sections have been attached to each other (e.g., welded to each other). If the shrink sleeving is applied prior to attaching the spiral sections 110, 111 to each other, the process of welding spiral sections 110, 111 together could damage the shrink sleeving, and thus covering 135. Furthermore, the presence of the shrink sleeving could make it difficult to weld spiral sections 110, 111 to each other.

The provision of a covering on the guide wire has the advantage of decreasing friction when the guide wire is inserted into the body vessel. Use of a shrink sleeving has the additional advantage that the covering, i.e., the shrink sleeving, serves as protection against breakage of the wire, in particular at the welding connection points between spiral sections 110 and 111 in the marking area. In addition, the length of the covering to be provided can easily be adjusted by selecting a shrink sleeving of a predetermined length.

What is claimed is:

1. A method for measuring a distance in the aorta and introducing a stent into the aorta, the method comprising:
   providing a guide wire, wherein the guide wire comprises a proximal end and a distal end, wherein the distal end comprises a spiral which has at least two adjoining spiral sections as markings, wherein at least a surface of one spiral section comprises a first material and at least a surface of the second spiral section comprises a second material, and further wherein the first material is different than the second material; and
   inserting the guide wire into the aorta;
   delivering the stent over the guide wire to the aorta such that the stent is disposed at a first location in the aorta; and
   measuring the distance between (i) the first location in the aorta, and (ii) a second location in the aorta, wherein the second location in the aorta is the location at which another blood vessel connects to the aorta, and wherein measuring is performed by counting the markings on the guide wire.

2. The method according to claim 1 further comprising introducing a contrast agent into the aorta.

3. The method according to claim 1 further comprising measuring a length of the stent while the stent is positioned in the aorta.

4. The method according to claim 1 further measuring a lesion in the aorta.

5. The method according to claim 4 wherein the lesion is at least one selected from the group consisting of a stenosis, an aneurysm, a rupture and a dissection.

6. The method according to claim 1 wherein at least a portion of the guide wire is provided with a covering.

7. The method according to claim 6 wherein the covering comprises polytetrafluoroethylene (PTFE).

8. The method according to claim 1 further comprising inserting a second guide wire into the aorta and delivering an implant over the guide wire to the aorta.

* * * * *